US005603958A

United States Patent [19]

Morein et al.

[11] Patent Number: 5,603,958
[45] Date of Patent: Feb. 18, 1997

[54] PHARMACEUTICAL CARRIER

[75] Inventors: Bror Morein; Karin Lövgren, both of Uppsala, Sweden

[73] Assignee: British Technology Group Limited, London, England

[21] Appl. No.: 455,403

[22] Filed: May 31, 1995

Related U.S. Application Data

[63] Continuation of Ser. No. 142,377, filed as PCT/SE92/00367, Jun. 1, 1992, abandoned.

[30] Foreign Application Priority Data

May 31, 1991 [SE] Sweden ................................ 9101665

[51] Int. Cl.⁶ ...................................................... A61K 9/16
[52] U.S. Cl. ............................................. 424/489; 424/484
[58] Field of Search ..................................... 424/450, 484, 424/489, 490

[56] References Cited

U.S. PATENT DOCUMENTS 4,900,549  2/1990  De Vries ................................. 424/88
5,077,057  12/1991  Szoka ..................................... 424/450
5,196,192  3/1993  Kretser .................................. 424/85.8

FOREIGN PATENT DOCUMENTS 0231039  8/1987  European Pat. Off. .
0415794  3/1991  European Pat. Off. .

OTHER PUBLICATIONS

Biotechnology and Applied Biochemistry, vol. 10, 1988, pp. 161–172.
Biochimica et Biophysica Acta, vol. 1062 (1991), pp. 165–171.

Primary Examiner—Gollamudi S. Kishore
Attorney, Agent, or Firm—Nixon & Vanderhye

[57] ABSTRACT

The invention refers to the use of an inert, structure-giving, deadjuvanated matrix of a complex of a sterol, such as cholesterol, and one or more saponins as a carrier for the administration of a pharmaceutically active substance, and a drug carrying particle comprising said inert structure-giving matrix to which has been connected a pharmaceutically active substance. The drug carrying particle, delpha, has an annular basic structure which can form spherical nano particles having a size of 30–50 nm and a narrow size distribution.

19 Claims, 6 Drawing Sheets

*Fig. 12*
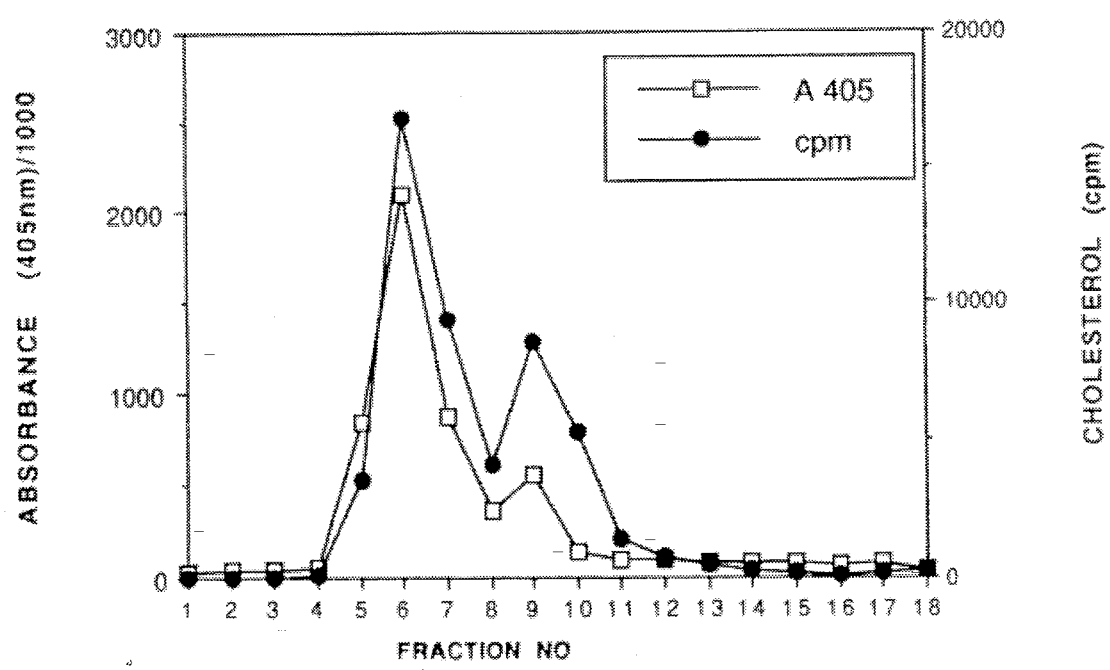
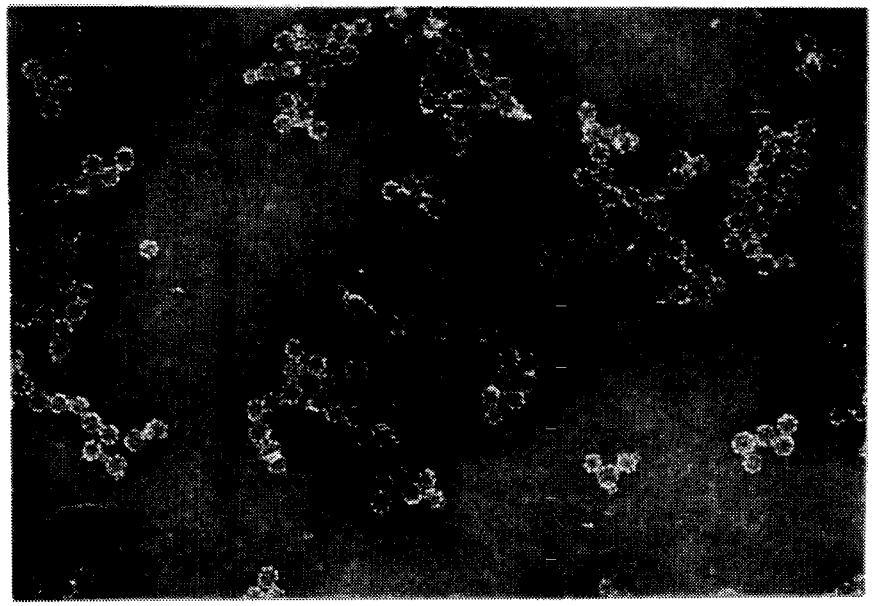
*Fig. 11*

PHARMACEUTICAL CARRIER

This is a Rule 62 continuation of application Ser. No. 08/142,377, filed Mar. 30, 1994, now abandoned.

The present invention refers to the use of nano particles as pharmaceutical carriers, drug carrying particles obtained by that and a pharmaceutical composition containing said particles.

BACKGROUND OF THE INVENTION

The use of colloidal particles of micrometer size as pharmaceutical carriers in different forms of administration has been the object of many investigations during the last decades. Lately, one has also succeeded in producing nano particulate carriers and demonstrated that they have large possibilities to facilitate the uptake of incorporated drugs.

In intravenous administration of colloidal particles they will be retrieved in different organs depending on the size and surface characteristics of the particles. Particles having a diameter larger than 7 µm are normally caught by the lung capillaries. Particles of the size 100 nm–5 µm are effectively eliminated by the reticuloendothelial system (RES), principally by the liver. This is a very fast process which normally gives the particles in the blood a half-life shorter than 1 minute. The rate of elimination can be strongly reduced if the surface of the particles is modified by being coated with substances making it hydrophilic.

Particles being smaller than 100 nm can theoretically, if they are not quickly eliminated by RES, leave the systemic circulation through gaps in the endothelium lining the inside of the blood vessels. Said gaps are of different size in different capillar beds. The endothelium in the pancreas, intestines and kidneys thus has gaps of 50–60 nm while the endothelium of the liver, spleen and bone marrow has gaps of about 100 nm. The blood vessels in certain tumours are also believed to have a more permeable endothelium allowing particles of nano size to pass into the tumour tissue. It has also recently been discovered that nano particles can penetrate the mucous membrane of the intestines, why they should be possible to use for obtaining a good absorption after oral administration of drugs which are sparingly soluble.

Pharmaceutical carriers in the form Of injectable nano particles have therefore been of great interest, especially for the administration of drugs to tumours, and sustained release of drugs and for the possibility to have an effect on the distribution in the body of the drug after intravenous injection.

Although a large number of different materials has been investigated with respect to the use as a matrix material for particulate pharmaceutical carriers there are only a few which have turned out to be of use for particles of nanometer size, i e certain liposomes, lipoproteins, especially Low Density Lipoproteins (LDL), and a few polymeric material, primarily polyalkylcyanoacrylate.

The use of said known nano particulate carriers is however associated with many problems. Liposomes are quickly eliminated by RES and are in addition fragile which brings about liposome formulations which are unstable and hard to handle. LDL is a material in short supply which is extracted from blood. In addition only very hydrophobic drugs can be incorporated without a first transformation into prodrugs. Polymeric pharmaceutical carriers are quickly eliminated by the RES and are in addition obtained in a broad size distribution which makes the control of the release of incorporated drugs more difficult.

Morein et al describe in WO 90/03184 an iscom-matrix consisting of a complex between at least one lipid, such a cholesterol, and one or more saponins for use as an immunomodulating agent. This matrix, which has the characteristic iscom structure, i e an open spherical structure having a diameter of about 40 nm formed from annular subunits having a diameter of about 12 nm, is said to have an adjuvant effect and is intended for use together with one or more antigens. In the same application is also demonstrated that the saponins in Quil A, an extract from the bark or Quillaja saponaria molina, can be divided into different substances, inter alia B2, B3 and B4b, some of which show adjuvant effect and others a structure giving effect. In Morein et al, Nature, Vol 308, No 5958, p 457–460 (1984) are for the first time described the immunostimulating complex, which are now commonly named iscoms, which have been formed between antigen determinants having hydrophobic areas and glycosides, such as triterpenesaponins and especially Quil A having an adjuvant effect, and which give an immunogenic effect 10–100 times higher than a normal mixture of antigen and Quil A.

DESCRIPTION OF THE INVENTION

It has now surprisingly turned out to be possible to use a particle of the same type as has previously been used as an adjuvant, as a carrier for the administration of drugs. The drug carrying particle in accordance with the invention does not comprise antigen or antigenic determinants and has if so proved to be immunologically inert. In addition should in general, in use as a pharmaceutical carrier, the adjuvant part be minimized; a use of the carrier with adjuvant component is however not excluded under the presumption that there will be no side effects. It can, however, be of importance that the adjuvant component is removed in connection with drugs of a protein or peptide type, as they might have epitopes initiating or stimulating to an immune response.

Adjuvant refers ideally to a substance which can be used for increasing the immunological response to another substance without initiating an immunological response to itself. In addition in this specification matrix=carrier refers to a structure giving complex between one or more saponins and cholesterol, which in addition optionally also contains other lipids, which can be immunologically inert or immunostimulating depending on the saponins which are included, having the form of spherical nano particles formed by annular subunits, deadjuvanated matrix refers to an immunologically inert matrix, iscom refers to matrix+antigen, an immunostimulating complex having the same particle structure as the matrix, delpha refers to matrix+drug, a drug carrying particle having the same structure as the matrix.

The present invention refers to the use an inert, structure giving deadjuvanated matrix of a complex of a sterol, such as cholesterol, and one or more saponins as a carrier for the administration of a drug, which matrix has an annular basic structure which can form spherical nano particles having a narrow size distribution.

According to a preferred aspect the matrix also comprises one or more other lipids, especially phospholipids.

The carrier particles preferably have a size of 30–50 nm, especially about 40 nm.

By the use of a carrier particle according to the invention the following is attained:

a narrow particle size distribution, which is of great importance in the administration of a drug in order to obtain a good reproducibility and uniform dosage;

a sustained duration in the circulation owing to a hydrophilic surface;

a high stability;

a possibility to bind amphiphilic and lipophilic pharmaceutical substances which are normally very sparingly soluble and hard to formulate.

The invention also refers to a drug-carrying particle comprising an inert structure-giving deadjuvanted matrix of a complex of a sterol, such as cholesterol, and one or more saponins as a carrier to which has been connected a pharmaceutically active substance, which particle has an annular basic structure capable of forming spherical nano particles of a narrow size distribution.

The drug carrying particle, delpha, normally has a size of 30–50 nm, especially about 40 nm.

It has turned out that a sterol, such as cholesterol, is necessary for the desired matrix to be formed. Useful sterols are in this context those who bind to saponins forming the wanted matrix structure, such as precursors and derivatives of cholesterol, as for example β-sitosterol, stigmasterol and thiocholesterol, the last mentioned of which can especially be used for binding a drug by means of the thiol moiety.

The saponins in question for the formation of complex is every structure forming saponin having hydrophobic areas such as those described in R Tschesche and Wulf, Chemie Organischer Naturstoffe, ed. W. Herz, H. Grisebach, G W Kirby, volume 30. (1973). Of special interest are very polar saponins, preferably polar triterpenesaponines such as polar acid bisdesmosides, e g saponin extract from Quillaja bark. Pure saponins without adjuvant effect are especially preferred, such as the substances obtained according to WO 90/03184 from an extract of Quillaja Saponaria Molina having 8–11 carbohydrate groups, i e B4b having a molecular weight of 1862, and optionally B2 having a molecular weight of 1988. The saponin fractions LT 15 and LT 17 have been obtained from the same extract by an alternative method based on a preparative column chromatographic procedure employing similar chromatographic conditions as the thin-layer analytical method described in WO 90/03184.

In addition to the sterol it is of advantage that the matrix comprises one or several other lipids. As example of lipids can be mentioned fats or fatty substances, such as triglycerides or mixed triglycerides containing fatty acids having up to 50 carbon atoms, e g butyric acid, caproic acid, capric acid, caprylic acid, lauric acid, myristic acid, palmitic acid, stearic acid, arachidic acid, behenic acid, lignoceric acid or unsaturated fatty acids having up to 30 carbon atoms such as hexadecenic acid, unsaturated hydroxy fatty acids; glycerol ethers, waxes, i e esters of higher fatty acids and monovalent alcohols; phospholipids such as derivatives of glycerolphosphates such as derivatives of phosphatidic acids i e lecitine, cephaline, inositolphosphatides, sphingosine derivatives having 14, 15, 16, 17, 18, 19 or 20 carbon atoms; glycolipids, isoprenoids, sulpholipids, carotenoids, steroids, sterols, cholestanol, caprostanol, phytosterols for instance stigmasterol, sitosterol, mycosterols, for instance ergosterol, bile acids for instance cholic acid, deoxycholic acid, kenodeoxycholic acid, litocholic acid, steroid glycosides, esters of vitamin A or mixtures thereof. Especially preferred are phospholipids, such as phosphatidylethanolamin, phosphatidylcholin.

It is of course desirable that the starting compounds used for preparing the carrier particles have a toxicity as low as possible. Owing to its stability the matrix which has been formed, however, normally shows a considerably lower toxicity than the sum of the included components.

As mentioned above the structure of delpha is identical to the structure of the matrix. By means of negatively stained electron microscopy an open spherical structure appears, having a diameter of 30–50 nm, especially 35–42 nm, being made up from more or less annular units having a diameter of 10–12 nm. On the enclosed electron micrographs FIGS. 1, 3 and 6 show different carrier matrices which can be used in accordance with the invention for the administration of pharmaceutically active substances. FIGS. 2, 4, 5 and 7 show less well defined complexes and FIG. 8 shows a defined $CoQ_{10}$-delpha. From this can be seen that all carrier matrices as well as the drug carrying particle show the same regular structure within a fairly narrow size interval.

A typical delpha consists of a cholesterol, one or more saponin components, such as B4b or a mixture of B4b and B2, a pharmaceutically active substance and a lipid, normally a phospholipid. Such a typical delpha having a particle size of 30–50 nm has a molecular ratio saponin: cholesterol:phospholipid: drug of 1:(0.1–10):(0–10):(0.1–50), wherein the saponin quotient consists of 10–100 % B4b and the remainder B2 and optionally other saponines. A normal delpha has a molecular composition of 1:1:0.5:0.5, the saponin being B4b.

For the preparation of a matrix or a delpha having annular particles of the size having a diameter of 10–12 nm the proportion between the different components saponin: cholesterol: phospholipid can be changed.

The structure giving matrix used as a carrier, as well as delpha, can be prepared in accordance with WO 90/03184 by solubilisation or transferring into a colloidal form of the sterol in a solvent, addition of the saponin or the saponins and optional additional additives, especially a pharmaceutically active substance, and then the solvent is removed or the concentration is decreases and the complex transferred to a solution in which the components thereof are not soluble, for instance an aqueous solution. This can be done by affinity chromatography, gelfiltration or centrifugation, ultrafiltration, dialyse, electrophoresis or by evaporation of the solvent or by decreasing the concentration of the solvent by dilution. The matrix and delpha, respectively, are then purified from the excess of sterol and saponins for instance by gelfiltration or centrifugation through a density gradient. As solubilizing agent can be used a detergent, such as a nonionic or ionic, such as cathionic or anionic or zwitterionic detergent, such as Zwittergent or a detergent based on bile acid used in excess. Typical examples are mentioned in WO 90/03184 mentioned above. The solubilizing agent is removed at conditions when the pharmaceutically active substance has sufficiently hydrophobic characteristics for being integrated into the delpha complex as formed. Some surfaceactive substances considerably facilitate the formation of the matrix. They comprise biological membrane lipids having a polar main group and a non-polar aliphatic chain, for instance phosphatidylcholine (negatively charged) and phosphatidylethanolamine (positively charged). The solubilizing agent can also be the solvent per se, such as alcohols, organic solvents or small amphiphatic molecules such as heptane-1,2,3-triol, hexane-1,2,3-triol, acetic acid or trifluoro acetic acid. Preferably ethylalcohol, dioxane, ether, chloroform, acetone, benzen, acetic acid, carbon disulfide, MEGA-10 (N-decanoyl-N-methylglucamine) and β-octylglucoside can be used.

In general it is necessary to remove the solubilizing agent from the matrix, which for instance can be done by dialysis, ultrafiltration, evaporation or column chromatographical technique. In certain cases it can also be possible after binding of the pharmaceutically active substance in question to dilute the obtained drug carrying particles to a concentration giving a physiologically acceptable solution.

The drug carrying particle in accordance with the invention can be prepared by incorporating a pharmaceutically active substance in the carrier matrix by hydrophobic interaction during the formation of the matrix complex as above, but also after the formation of the carrier material. The pharmaceutically active substance can in addition to hydrophobic interaction be linked to the carrier matrix by chemical coupling in a way known per se to a suitable functional group which has been integrated into a previously formed matrix.

As an example of functional groups suited for binding the pharmaceutically active substance can be mentioned —$NH_2$, —SH, —COOH, —OH. A number of groups and methods of coupling are described in Journal of Immunological Methods, 59 (1983), 129–143, 289–299; in Methods of Enzymology, volume 93, p 280–333; and in Analytical Biochemistry 116, p 402–407 (1981).

Pharmaceutically active substances which can be incorporated into a carrier matrix in accordance with the invention may be of varied composition and size. They are either to be incorporated as solitary units or in combination with other molecules. The binding can occur by means of hydrophobic interaction or through a covalent binding. As an example can be mentioned large glycoproteins having a molecular weight of up to 400 kd and oligopeptides with some few amino acids that can be bound by hydrophobic interaction. Also native proteins, triterpenoids and flavines etc can be incorporated through hydrophobic interaction. Certain substances, for instance a number of proteins, poly- and oligopeptides can be incorporated through hydrophobic interaction after the hydrophobic regions having been exposed by various treatments of a denaturating character. Non-hydrophobic molecules can be incorporated into delpha complexes through covalent bindings to incorporated lipophilic components, for instance phosphatidyl-ethanolamine or covalent bindings to sugar, aldehyde etc.

The invention also refers to a pharmaceutical composition comprising drug carrying particles as above in combination with a pharmacologically acceptable vehicle. Many conventional pharmaceutical vehicles normally being part in different types of drugs can be used. The delpha particles can for instance be suspended in aqueous solutions or be freeze-dried in the formulations. As example of types of drugs containing delpha the following can be mentioned:

injection fluids, injection and infusion substances and implant tablets for parental administration.

"solutions", gels, ointments and creams for topical administration.

capsules, tablets, dragées and mixtures for oral administration.

The concentration of delpha in the different formulations of drugs may vary depending on the included drugs and the way of administration. Normally 1 ml or 1 g of pharmaceutical formulation may contain 0.01–100 mg delpha.

The drug carrying particle in accordance with the invention, delpha, can be used in peroral and parenteral administration of pharmaceutical substances. Furthermore, the delpa can be used for topical administration, for instance via the eye, nose and skin, of pharmaceutical substances intended for systemic effect. Also very sparingly soluble pharmaceutical substances can be incorporated into delpha. An example of a substance extremely difficult to dissolve is coenzyme $Q_{10}$, as well as nifedipine, which today are not available on the market as an injection liquids due to their solubility characteristics. There are other substances difficult to dissolve in the groups of corticosteroids and steroid hormones. Furthermore there are certain cytostatics, for instance ethoposide, that are sparingly soluble.

Delpha can also be used for parenteral administration of drugs with a short biological half-life. These must be administrated by giving repeated injections, as oral administration is impossible due to enzymatic degradation. A sustained release of said drugs from a delpha particle would make possible fewer injections. As examples of pharmaceutically active substances can be mentioned insulin, growth-hormone, calcithonine, GHRH (growth-hormone-releasing hormone).

Another preferred field of use for the drug carrying particles according to the invention is for parenteral target controlled administration of drugs, especially cytostatica.

In the drug carrying particle, delpha, components may be part of several combinations with different molecules and in this connection it has been shown that the components included have been incorporated by tested cells (macrophages and cells from the cell line Wehei 110). With immunofluorescence and electron microscopy it has been possible to follow the complex into the cell, while micells of the corresponding protein have been disintegrated. Consequently this means that the delpha particles are very stable. The uptake and transportation from the injection site is rapid and the components bound to the carrier matrix according to the invention are transported to different organs, such as for instance draining lymphatic organs. After intraperitoneal administration a comparatively large amount of the components are to be found in the spleen. Other organs are the heart, liver, bile, spleen, kidneys, ureter and urine bladder, lungs. A combination of different components in one and the same particle may imply synergism, as different components may have different tasks; one component may for instance target a certain organ or type of cell or for the penetration of mucous and another component may influence the cell. The components in such a complex can be taken up by one and the same cell which is to be influenced.

The carrier matrix according to the invention, as well as a delpha formed in the same way, is characterized in that neither an antibody mediated immunity (AMI) nor a cell mediated immunity (CMI) is developed against the components included therein. Since no immune response is developed against the carrier matrix it can be used as a carrier for various drugs on repeated occasions without immunological reactions preventing for instance a penetration of mucus in local application in for instance the nose, the conjunctive or per os, or prevent adsorption and further distribution of the carrier or delpha and drugs incorporated therein in the organism in parenteral application. Immunological reactions causing secondary effects can thus be avoided.

For the preparation of a pharmaceutical composition a kit can be provided, comprising separate packages of particles of a structure-giving matrix according to the invention, optionally in combination with a surface-active substance, and a pharmacologically acceptable vehicle.

BRIEF DESCRIPTION OF THE DRAWINGS

The invention is furthermore illustrated by the following examples of the preparation and use of a structure giving carrier matrix and drug carrying particles under reference to the enclosed drawings.

FIG. 11 shows in a magnification of about 75,000 an electron micrograph of delpha particles containing amfotericin B, which have been prepared in accordance with example 6d); and FIG. 12 refers to the absorbance and counts respectively of different fractions obtained in analysing the delpha particles displayed in FIG. 11.

EXAMPLES

Figure 1:
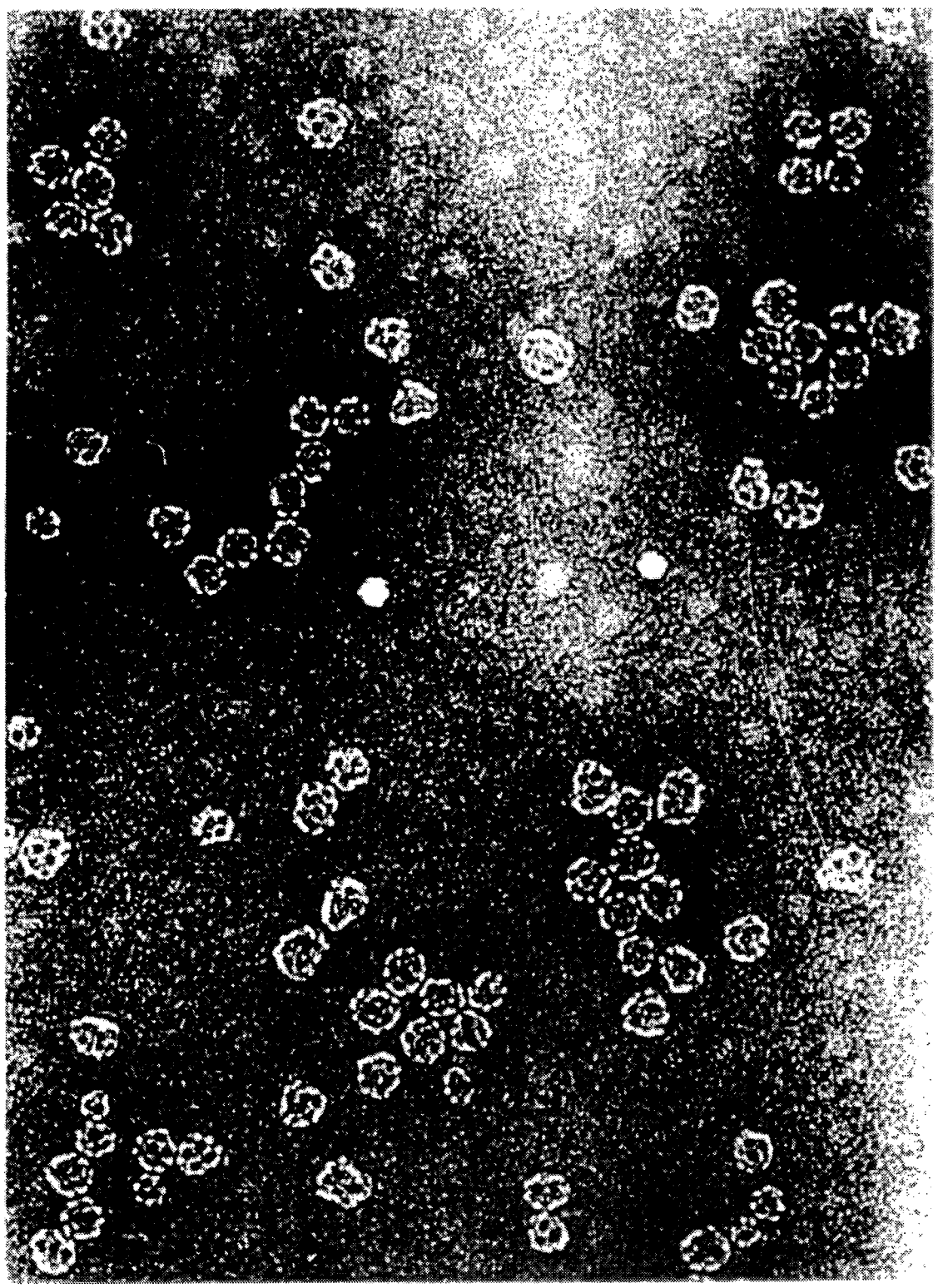
FIG. 1 shows in a magnification of 200,000 an electon micrograph of a carrier matrix of the invention as prepared in example 2 from Quil A, cholesterol and phosphatidylethanolamine.

In the following examples, No. 1–4 refer to the preparation of carrier particles to which a desired drug can be covalently coupled; No. 5–6 refer to a direct preparation of delpha particles, that is particles wherein a drug has been incorporated into the matrix by hydrophobic interaction; and No. 7–8 refer to the preparation of delpha particles wherein the drug has been covalently coupled to the carrier matrix.

EXAMPLE 1

Delpha carrier

A carrier for non-hydrophobic pharmaceuticals is prepared as follows. 1000 µl lipid-mix consisting of 10.0 mg cholesterol (+ traces of $^3$H-cholesterol), 10.0 mg phosphatidylethanolamine and 200 mg MEGA-10 (N-decanoyl-N-methylamine) in $H_2O$ are mixed with 500 mg LT15 (a saponin fraction obtained from Karlshamns Lipidteknik AB, Stockholm, Sweden) dissolved in $H_2O$ (10 % w/w) and the volume is adjusted to 5–10 ml with PBS (0.02M phosphate buffered saline, 150 mM NaCl, pH 7.4). The mixture is incubated on a shaker for 4–24 hrs before it is dialysed against 5×5 l PBS (ambient temperature for 24–48 hrs., thereafter at +4° C.).

The formed carrier complexes are purified from excess material on a sucrose gradient, 10–50% w/w, 18 hrs., 400,000 rpm (rotor TST 41.14), 10° C. The gradient is emptied from below in 17 fractions which are analysed as to carrier particles ($^3$H-cholesterol and electron microscopy, EM) according to the table 1 below. Fractions containing carrier particles are pooled and the exact amount of the included components (cholesterol, phosphatidylethanolamine and saponin) are determined. The carrier particles can for example be concentrated by pelleting (18 hrs., 40,000 rpm (TST 41.14), 10° C.). A pelleted carrier is dissolved to a requested concentration of for example 10 mg/ml, in a suitable buffer and is stored at a temperature of +4° C. (1 month) or –70° C. (long-term storage) until use.

TABLE 1

| Fraction No. | Cholesterol (cpm) | Particles (EM) |
| --- | --- | --- |
| 1 | 30 | – |
| 2 | 20 | – |
| 3 | 27 | – |
| 4 | 41 | – |
| 5 | 246 | + |
| 6 | 11807 | +++++ |
| 7 | 6802 | ++++ |
| 8 | 2577 | +++ |
| 9 | 968 | ++ |
| 10 | 570 | + |
| 11 | 471 | (+) |
| 12 | 329 | – |
| 13 | 275 | – |
| 14 | 197 | – |
| 15 | 139 | – |
| 16 | 315 | – |
| 17 | 576 | – |

The same effect is obtained if LT 15 is replaced by a mixture of LT 15 and LT 17.

EXAMPLE 2

Delpha carriers

A carrier for non-hydrophobic pharmaceuticals is prepared as follows. 1000 µl lipid-mix, consisting of 10.0 mg cholesterol (+ traces of $^3$H-cholesterol), 10.0 mg phosphatidylethanolamine and 200 mg MEGA-10 (N-decanoyl-N-methylglucamine) in $H_2O$ are mixed with 500 mg Quil A (Spikosid, from Iscotec, Luleå) dissolved in $H_2O$ (10% w/w), the volume is adjusted to 5–10 ml with PBS (0.02M phosphate buffered saline, 150 mM NaCl, pH 7,4). The mixture is incubated in shaking for 4–24 hrs before it is dialysed against 5×5 l PBS (ambient temperature for 24–48 hrs, thereafter +4° C.). The carrier particles can be concentrated, analysed and stored according to example 1. The result of the analyses is given in Table 2 below.

TABLE 2

| Fraction No. | CPM (3H-cholesterol) | EM (matrix structure) |
| --- | --- | --- |
| 1 | 59 | |
| 2 | 54 | |
| 3 | 71 | |
| 4 | 2562 | ++ |
| 5 | 22801 | +++ |
| 6 | 44101 | +++ |
| 7 | 17900 | +++ |
| 8 | 5717 | +++ |
| 9 | 2394 | ++ |
| 10 | 1471 | + |
| 11 | 970 | |
| 12 | 732 | |
| 13 | 513 | |
| 14 | 676 | |
| 15 | 408 | |
| 16 | 353 | |
| 17 | 690 | |

FIG. 1 shows in a magnification of 200,000 times the carrier matrix of fraction 5, viz. the spherical association complexes of a size of 30–50 nm in diameter, formed from an annular basic structure having a diameter of approximately 10 nm.

The same effect is achieved if instead of Quil A is used 250 mg of each of B2 and B4b, or 500 mg pure B4b.

EXAMPLE 3

Delpha carriers

A carrier matrix for non-hydrophobic drugs is manufactured as in example 2 by mixing 100 µl of a solution consisting of 1.0 mg stigmasterol and 20 mg MEGA-10 in $H_2O$ with 5.0 mg Quil A.

Figure 2:
FIG. 2-4 show in a magnification of about 75,000 electron micrographs of three other carrier matrices prepared in accordance with example 3 from Quil A and three different sterols, that is stigmasterol, β-sitosterol and lanosterol.

The mixture is incubated on a shaker for 4–24 hrs before it is dialysed against PBS (ambient temperature for 24–48 hrs, thereafter +4° C.). The EM verifies that carrier complexes have been formed. Formed complexes are purified on a sucrose gradient 10–50% w/w for 18 hrs at 40,000 rpm (rotor TST 41,14) at 10° C. or by sedimentation through 20% w/w sucrose for 18 hrs at 40.000 rpm (rotor TST 41,14) at 10° C. Sedimented complexes are dissolved in PSB. FIG. 2 shows in a magnification of 75.000 the obtained basic structure, here as partially associated.

Figure 3:
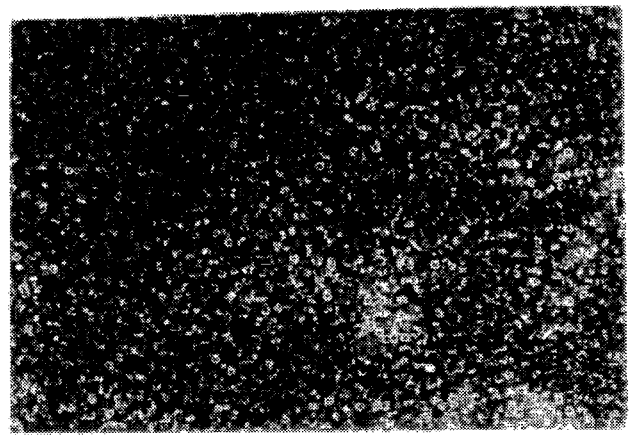
Figure 4:
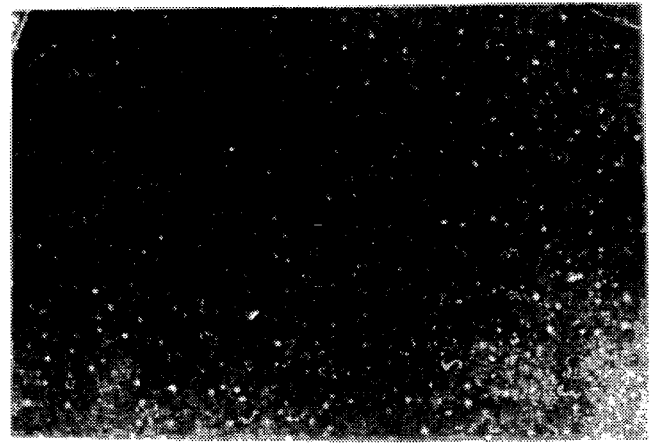

If stigmasterol in the example above is replaced by β-sitosterol monomer carrier particles of an annular basic structure (10–12 nm) is obtained, as is shown in FIG. 3. If stigmasterol instead is replaced by lanosterol the basic structure is obtained in another associated form according to FIG. 4.

If Quil A in this example is replaced by LT 15 or a mixture of LT 15 and LT 17 similar structures are obtained.

EXAMPLE 4

Delpha carriers

Figure 5:
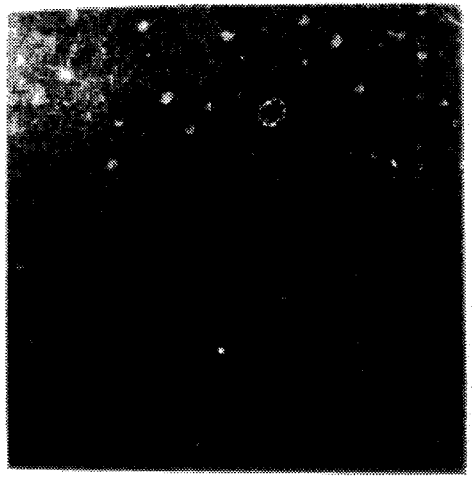
FIG. 5-7 show in a magnification of about 75,000 electron micrographs of three other carrier matrices as prepared in example 4 from Quil A, phosphatidylcholine and one of stigmasterol, β-sitosterol and lanosterol respectively.

A carrier matrix for non-hydrophobic drugs prepared is in accordance with example 2 from 100 µl of a solution consisting of 1.0 mg stigmasterol, 1.0 mg phosphatidylcholine and 20 mg MEGA-10 in $H_2O$ mixed with 5.0 mg Quil A. The mixture is incubated in a shaker for 4–24 hrs before being dialysed against 5×5l PBS (ambient temperature 24–48 hrs, then +4° C.). The fact that carrier complexes are formed is verified by EM. Formed complexes are purified on a sucrose gradient 10–20% w/w for 18 hrs at 40,000 rpm (rotor TST 41,14) at 10° C. or through/by sedimentation through 20% w/w sucrose for 18 hrs at 40,000 rpm (rotor TST 41,14) at 10° C. Sedimented complexes are dissolved in PBS. FIG. 5 shows in a magnification of 75,000 times an electromicrograph of the obtained honeycomb structure.

Figure 6:
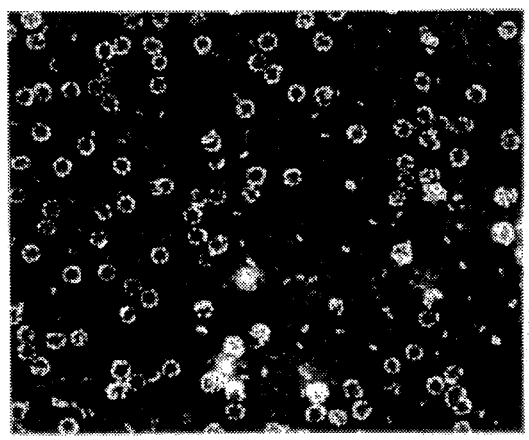
Figure 7:
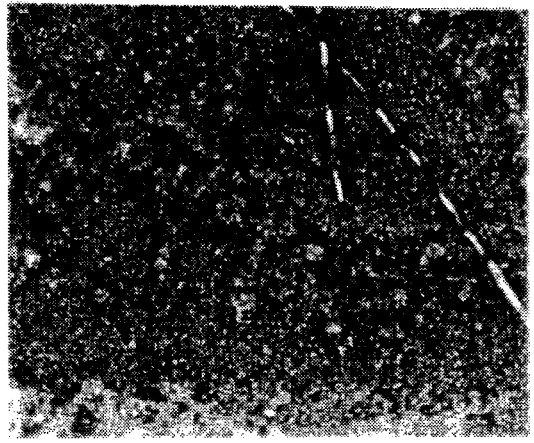

If, on the other hand, stigmasterol in the above example is replaced by β-sitosterol spherical carrier particles in accordance with FIG. 6 are obtained with a structure similar to the one shown in FIG. 1. If stigmasterol instead is replaced by lanosterol the main part of the material is precipitated, see FIG. 7.

These examples show that from the tested sterols stigmasterol presented the "best" preparation, that is a transparent solution without precipitation in the absence of phospholipid. The lanosterol and the β-sitosterol brought about a lesser precipitation in addition to the complexes shown on the EM photograph. When phospholipid was added the solution with lanosterol and stigmasterol, respectively, became opalescent, which indicates that a great part of the material did not form any complex with Quil A. β-sitosterol on the other hand formed a well-defined matrix with Quil A and phospholipid.

EXAMPLE 5

CoQ$_{10}$-delpha 2 mg $CoQ_{10}$ are dissolved in about 25 µl chloroform and mixed with a 400 µl lipid-mix, consisting of 4.0 mg cholesterol (+ traces of $^3$H-cholesterol), 4.0 mg phosphatidylcholine and 80 mg MEGA-10 in $H_2O$. The chloroform is evaporated by a gentle nitrogen bubbling while vigorous stirring of the mixture. The temperature is kept at 25°–35° C. When the chloroform has been removed 10 mg Quil A (Spikosid) dissolved in $H_2O$ (10% w/w) is added, the volume is adjusted to 2 ml with PBS [phosphatbuffered (0.02M), 150 mM NaCl, pH 8.4}. The mixture is incubated in shaking for 2–4 hrs (in darkness), before being dialysed against 3×5 l PBS (in darkness, ambient temperature).

The formed $CoQ_{10}$-carrying particles are purified from excess material on a sucrose gradient, 10–50% w/w, 18 hrs, 40.000 rpm TST 41,14), 10° C. The gradient is emptied from below in 17 fractions which is each analysed as to the $CoQ_{10}$ (A330) and delpha particles ($^3$H-cholesterol and electron microscopy). Fractions containing $CoQ_{10}$-delpha are pooled and the exact concentration of $CoQ_{10}$ is determined. $^3$H-cholesterol is determined by taking 50 µl samples from each fraction in the gradient, mixing with 4 ml scintillation fluid (optiphase Hisafe II, Pharmacia-LKB) and counting for 60 seconds in a β-counter (Rackbeta, LKB). The result is shown in Table 3 below.

TABLE 3

| Fract. No. | CPM (3H-cholesterol | A330 (CoQ$_{10}$) | EM (matrix structure) |
|---|---|---|---|
| 1 | 22 | 0.055 | – |
| 2 | 23 | 0.056 | – |
| 3 | 32 | 0.053 | – |
| 4 | 30 | 0.081 | – |
| 5 | 25 | 0.080 | – |
| 6 | 1410 | 0.149 | + |
| 7 | 12120 | 0.653 | +++ |
| 8 | 9624 | 0.397 | +++ |
| 9 | 3600 | 0.167 | ++ |
| 10 | 1513 | 0.124 | + |
| 11 | 1578 | 0.289 | + |
| 12 | 1023 | 0.382 | (+) |
| 13 | 507 | 0.357 | – |
| 14 | 408 | 0.213 | – |
| 15 | 437 | 0.384 | – |
| 16 | 275 | 0.499 | – |
| 17 | 294 | 1.225 | – |

Figure 8:
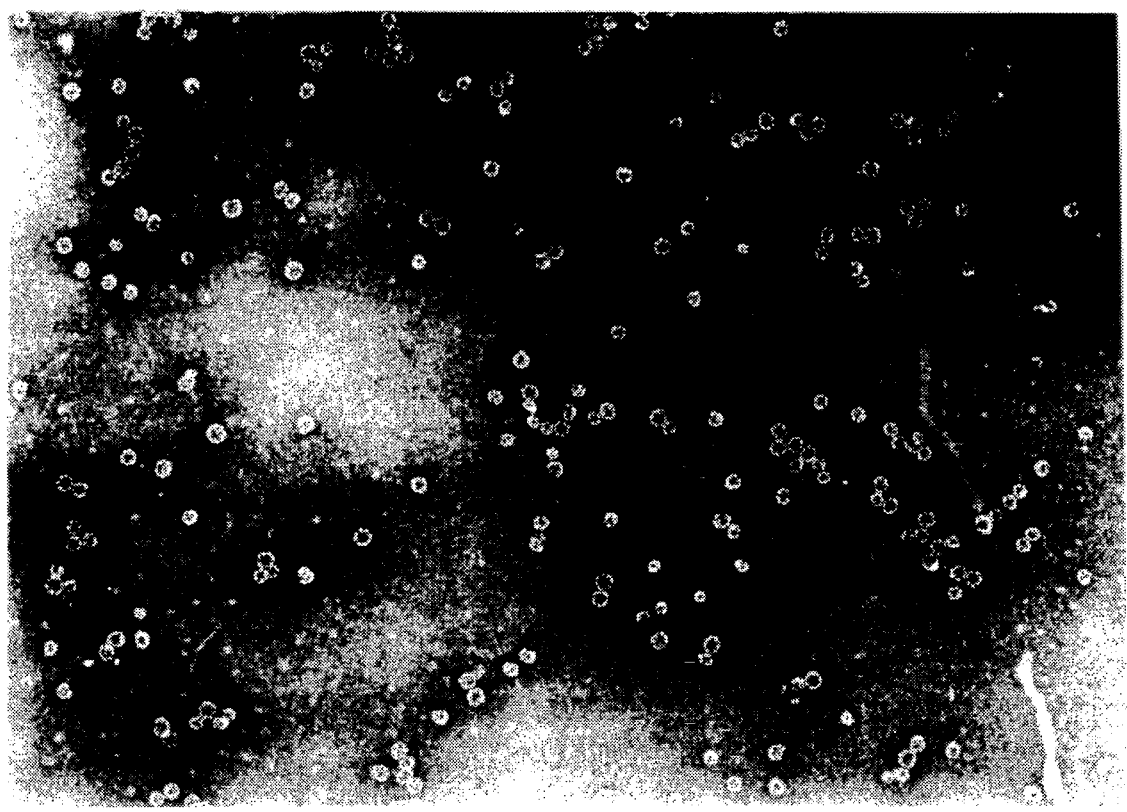
FIG. 8 shows in a magnification of about 75,000 an electron micrograph of delpha particles containing $CoQ_{10}$, prepared in accordance with example 5.

FIG. 8 shows in a magnification of 1:75,000 an electron migrograph of the delpha structure obtained in fraction 7, 30–50 nm, similar to the photograph in FIG. 1.

The same result is obtained if instead of Quil A 5 mg of each of B2 and B4b are used.

EXAMPLE 6

Amfotericin B delpha

In order to prepare amfotericin B delpha particles 1 mg amfotericin B was dissolved in 75 µl DMSO and mixed with a) 2 mg of each of cholesterol and phosphatidyl choline and mixed with 10 mg B4b (LT 15);

b) 3 mg of each of cholesterol and phophatidyl choline and mixed with 15 mg B4b (LT 15);

c) 2 mg of each of cholesterol and phosphatidyl choline and mixed with 8 mg B4b (LT 15) and 2 mg B2 (LT 17); or d) 3 mg of each of cholesterol and phosphatidyl choline and mixed with 12 mg B4b (LT 15) and 3 mg B2 (LT 17); in a volume of 1 ml PBS. The complexes were made and analyzed as described in example 1.

The fractions obtained form sucrose density gradient centrifugation were analyzed for cholesterol (cpm), absorbance at 405 nm (amphotericin B) and structure (EM) and showed that amphotericin B efficiently incorporated into delpha particles. The use of ony LT 15 and amfotericin B produces a somewhat aggregated delpha, an addition of LT 17 helped to give non-aggregated particles.

Figure 10:
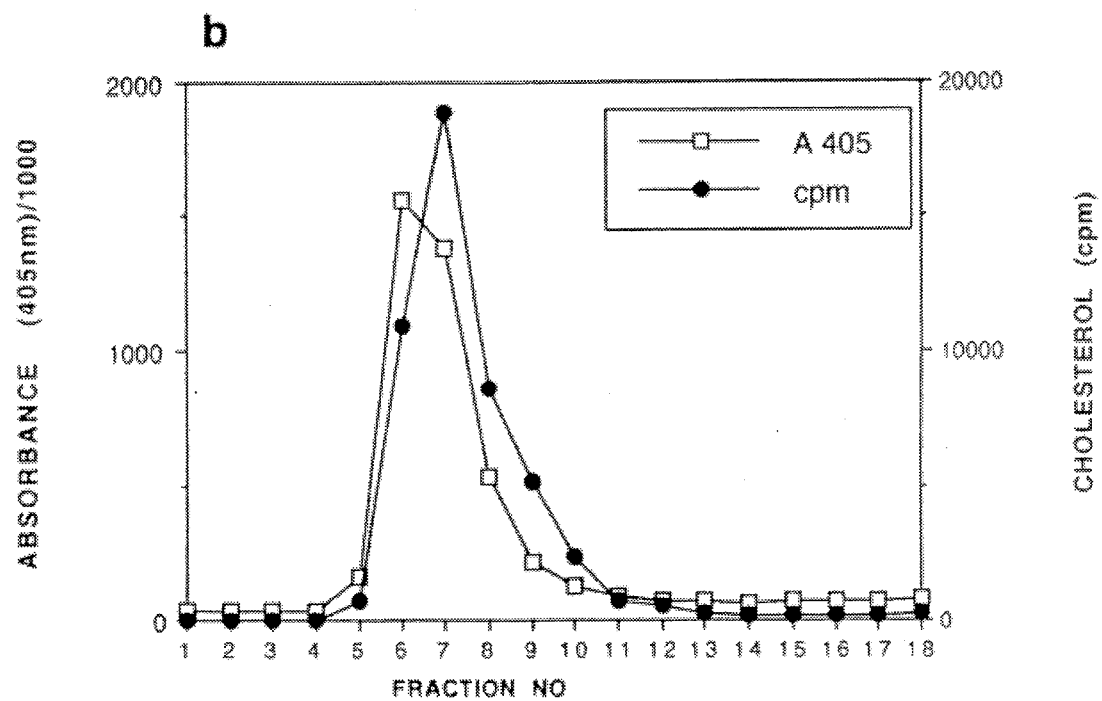
FIG. 10 refers to the absorbance and counts respectively of different fractions obtained in analysing the delpha particles displayed in FIG. 9.
Figure 9:
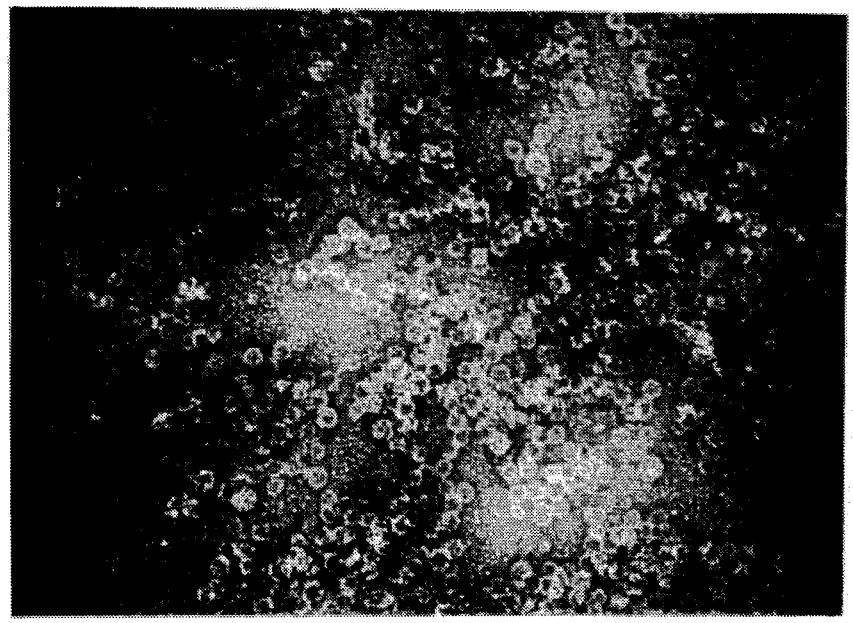
FIG. 9 shows in a magnification of about 75,000 an electron micrograph of delpha particles containing amfotericin B, which have been prepared in accordance with example 6b)

FIG. 9 shows an electron micrograph of amfotericin B delpha particles prepared according to method b) above in a magnification of about 75,000;

FIG. 10 shows a graph of the absorbance and counts respectively obtained from the analysis of the different fractions obtained from the amfotericin B delpha particles prepared according to said method b);

FIG. 11 shows an electron micrograph of amfotericin B delpha particles prepared according to method d) above in a magnification of about 75,000;

FIG. 12 shows a graph of the absorbance and count respectively obtained from the analysis of the different fractions obtained from the amfoteracin B delpha particles prepared according to said method d).

A larger proportion of LT 17 will give an increased amount of sub units (10–12 nm), which on the graph in FIG. 12 can be seen as a second peak.

EXAMPLE 7

LHRH-delpha

LHRH (luteinizing hormone releasing hormone) is conjugated to the carrier matrix in accordance with the principles for conjugation via cysteine by means of maleidohexanoylN-hydroxysuccinimidester (MHS), described by Lee et al, Molecular Immunology, Vol. 17, pages 749–756 (1980).

The peptide is reduced according to the following. 1 mg peptide is dissolved in 400 µl 0.1M sodiumphosphate buffer pH 8.0. A 250×molar excess of dithiotreitol (DTT) is added and the mixture is incubated at ambient temperature for 30–60 minutes. The peptide is separated from DTT by gelfiltration on Sephadex G-10 (Pharmacia, Uppsala) equilibrated with deaired $N_2$Saturated 0.1M sodiumphosphate buffer pH 6.66, containing 0.1M EDTA.

The carrier matrix according to example 2 is MHS modified as follows: 2.0 mg carrier in 450 µl 0.1M sodiumphosphate buffer, pH 6.66, is mixed with 10–100×molar excess of MHS (in 50 µl DMSO) to phosphatidylethanolamine in the matrix. The reaction mixture is stirred gently at ambient temperature for 1 hour. Excess of MHS and other reaction products are removed through gelfiltration at Sephadex G-25 (Pharmacia, Uppsala) equilibrated with deaired $N_2$saturated 0.1M sodiumphosphate buffer pH 6,66, containing 0,1M EDTA. The solution with reduced peptide is mixed with MHS activated carrier in a 5×molar excess ratio of peptides to phosphatdylethanolamine. The conjugation is allowed to continue during stirring for 18–24 hours.

LHRH-delpha is purified from excess material on a sucrose gradient, 10–50% w/w, 18 hrs, 40.000 rpm (TST 41.14), 10° C. The gradient is emptied from below in 17 fractions which each is analysed as to LHRH and delpha particles ($^3$H-cholesterol and electron microscopy). Fractions containing LHRH-delpha particles are pooled and the concentration is determined.

EXAMPLE 8

Biotin-delpha 1 mg (2.0 mg/ml) carrier (made according to example 2) in 0.1M carbonate buffer, pH 8.8, is mixed with N-hydroxysuccinimidebiotin (10 mg/ml in DMSO) in an excess of 10×1 in relation to phosphatidylethanolamine. The mixture is incubated for 15 minutes at ambient temperature. The biotin-delpha-particles are purified from surplus material on a sucrose gradient, 10–50% w/w, 18 hrs, 40,000 rpm (TST 41,14), 10° C. The gradient is emptied from below in 17 fractions which each is analysed as to LHRH and delpha particles ($^3$H-cholesterol and electronmicroscopy), see Table 4 below, and biotin. Fractions containing biotin-delpha particles are pooled and the quantity is determined.

TABLE 4

| Fract. No. | CPM (3H-cholesterol) | EM (matrix structure) |
|---|---|---|
| 1 | 45 | − |
| 2 | 22 | − |
| 3 | 41 | − |
| 4 | 24 | − |
| 5 | 1314 | + |
| 6 | 14993 | ++ |
| 7 | 26315 | +++ |
| 8 | 8239 | ++ |
| 9 | 3644 | ++ |
| 10 | 1704 | + |
| 11 | 1024 | |
| 12 | 673 | |
| 13 | 523 | |
| 14 | 321 | |
| 15 | 230 | |
| 16 | 170 | |
| 17 | 154 | |

A pool consisting of the fractions 5–10 is analyzed for biotin in an ELISA.

Coat: mouse anti-biotin (monoclonal) 10 g/ml in a 50 mM carbonate buffer, pH 9.6, 4° C. over night.

Dilution tests (pool and non-biotinylated matrix): 1/50, 1/150, 1/450 etc in PBS Tween (0.05%), 1 hr, ambient temperature, on a shaker.

Conjugate: avidine-HRP (horse-radish peroxidase) 1/2000 in PBS Tween (0,05%), 1 h, ambient temperature, on a shaker.

Development: TMB (tetramethyl benzidine) 0.10 mg/ml and $H_2O_2$ (0.006%) in 0.1M acetate, pH 6.0.

TABLE 5

| Dilution test | ABS (pool) | ABS (control matrix) |
|---|---|---|
| 1/50 | 1.997 | 0.097 |
| 1/150 | 2.107 | 0.078 |
| 1/450 | 1.874 | 0.106 |
| 1/1350 | 1.201 | 0.099 |
| 1/4050 | 1.816 | 0.100 |
| 1/12150 | 0.206 | 0.089 |
| 1/36450 | 0.096 | 0.090 |
| 1/109350 | 0.103 | 0.115 |

The following test shows the distribution of drug in the body after administration by means of a delpha according to the invention.

Biological tests to show that the carrier is immunologically inert

LT 15

LT 15 is an adjuvant depleted fraction of Quil A which has been obtained from Karlshamns Lipidteknik AB.

A conventional saponin adjuvant, like Quil A, potentiates the immune response to an antigen when mixed with the antigen prior to e.g. subcutaneous injection. To confirm that LT 15 (which is very similar to the B4b preparation) is depleted of adjuvant active saponins the following test for adjuvant activity was performed in mice.

3 groups of 5 mice were immunized with 1 μyg of protein micelles made from influensa virus glycoproteins (L övgren et al 1987) plus:

a) 10 μyg LT 15
b) 10 μug Quil A
c) saline

Two weeks after immunization the mice were bled and the serum was assayed for antibodies to the viral proteins (standard Elisa technique employing microtine plates coated with the antigen and a commercial enzyme-conjugated rabbit anti-mouse preparation for detection of mouse immunoglobulins). The result shown in table 6 below demonstrates that LT 15 as well as plain saline did not potentiate the antibody response to the protein micelles in contrast to the non-depleted Quil A preparation.

TABLE 6

| Group | Amount of antibody (arbitrary unit) |
|---|---|
| a) | 714 +− 397 |
| b) | 1055 +− 347 |
| c) | 800 +− 367 |

Different biotin-carriers

The administration of biotin to mouse using different carriers. In order to verify that the carrier matrix is immunologically inert when used as a drug carrier a comparative test was made with biotin administered as biotin-delpha and with immunologically active carriers. Mice were injected subcutaneously with biotin carried by immunologically active carriers—iscom and micelle respectively—containing surface proteins from an influensa virus. After an immunization with 3 μg carrier-biotin all mice had high (iscom) or medium high (micelle) serum titres against biotin. Eight weeks later the mice were given a "booster-dose" with biotin-delpha-particles. Two weeks later serum samples were taken and the amount of antibodies against biotin before and after the administration of the biotin-delpha was compared. A control group of animals was injected with biotin-delpha on both occasions. As appears from Table 7, the administration of biotin-delpha had no effect on the antibody response against biotin not even in those cases when the animals had been primarily immunized against biotin linked to an immunologically active carrier. After a booster with an active carrier the serum titres against biotin were increased 5–10 times (not shown in Table 7).

TABLE 7

| Primary administration | | Secondary administration | |
|---|---|---|---|
| biotin-formulation | antibody response against biotin | biotin-formulation | antibody response against biotin |
| biotin-iscom (33 mice) | 2999 ± 467 (1824–3781) | biotin-delpha (11 mice) | 3101 ± 317 (2301–3476) |
| biotin-micelle (33 mice) | 973 ± 470 (291 ± 1971) | biotin-delpha (11 mice) | 850–486 (398–1978) |
| biotin-delpha (34 mice) | 59 ± 13 (42–89) | biotin-delpha (11 mice) | 49 ± 5 (42–57) |

Autoradiography of $CoQ_{10}$-delpha in mouse

Delpha-particles were prepared by 1 mg $CoQ_{10}$, 2 mg $^3H$-cholesterol, 2 mg phosphatidylcholin, 10 mg MEGA-10 and 10 mg LT 15 in a volume of 1 ml $H_2O$ according to example 5. The fractions 5–7 were pooled and the content of cholesterol was determined by means of the $^3H$-activity to be 0.73 mg cholesterol/ml. The content of $CoQ_{10}$ was estimated to $\leq 0.1$ mg/ml.

4 female mice were injected subcutaneously in the neck with 0.4 ml of the mixture above. The mice were sacrified and sectioned for autoradiography after 15 min, 2 h, 6 h and 24 h.

After 24 h particles were still present at the site of injection, which indicates that the cholesterol is linked to the particles. Compared with administration of free cholesterol high levels of cholesterol were found in the liver and in the blood; still more in the lungs; and still more in the spleen, bone marrow and local lymphatic organs. It was observed that the level in the blood increased continuously up to 24 h.

From this can be concluded that the cholesterol mainly is particle-bonded; if pure cholesterol is injected there will be a concentration of cholesterol in the adrenal cortex.

Administration of $CoQ_{10}$ to mouse

The length of the isoprene chain in the Coenzyme Q (CoQ) varies in different animal species. $CoQ_9$ thus contains 9 isoprene units in the chain and $CoQ_{10}$ contains 10 units. Man only produces $CoQ_{10}$ whereas the rat and mouse produce about 95% $CoQ_9$ and 5% of $CoQ_{10}$. Due to the low endogene concentration of $CoQ_{10}$ mouse was chosen as for the experiment in the following test:

15 NMRI mice (females) 19.20g±0.90 g were injected subcutaneously with 14.6 μg $CoQ_{10}$-delpha (0.8 mg/kg) made with B2+B4b instead of Quil A according to example 5, i e with 0.2 ml of a formulation containing 73 μg/ml $CoQ_{10}$. At T=0, 0.5, 1, 3, 5 and 8 hours blood samples were taken and at T=0, 0.5, 3 and 8 hours organs were also removed (heart, liver, kidneys and spleen). To measure the endogene level a control group of 6 (mice) were injected with empty delpha complexes, i e only carriers in a corresponding amount. Blood samples and organs were taken from this control group at T=0.5 and 7 hours. As a comparison serum and organs were taken also from 3 non treated mice. The blood was centrifuged and plasma and organs were kept at a temperature of −20° C. until analysed. The chemical analyses of $CoQ_{10}$ were carried out with liquid chromatography in accordance with a method described by P-O Englund in J. Chromatogr. 425 (1988), 87–97. The organ samples were homogenised with a Potter-S homogenisator in 10 volumes 1-propane containing an intern standard. The liquid phase was injected into the liquid chromatograph. The chemical analyses showed an increase of the $CoQ_{10}$ content in serum and heart, see table 8. To analyse cholesterol a sample, 1 ml, from the liquid phase is mixed with 8 ml scintillation fluid (Orphphase Hisafe II, Pharmacia LKB) and is counted for 2000 seconds in a β-counter (Rackbeta, LKB). In measuring the radioactivity in the organ samples ($^3$H-cholesterol) a distinct radioactivity was registered only in liver samples.

The following can be concluded from the experiment:

since the $CoQ_{10}$ part is continuously increased in serum for 8 hours, and probably longer, the delpha complexes have not immediately been eliminated by RES the delpha-complex is supposed to have delivered $CoQ_{10}$ to the heart as $CoQ_{10}$ in the heart tends to increase without a corresponding increase of the cholesterol of the complexes being found the delpha complexes and/or included cholesterol are likely to be eliminated via the liver which demonstrated the highest degree of radioactivity.

TABLE 8

| Mouse No | Time h | Spleen μg/g | Kidney μ/g | Liver μ/g | Heart μg/g | Serum μg/m |
|---|---|---|---|---|---|---|
| 1 (contr.) | 0.5 | 6.770 | 11.500 | 3.050 | 21.000 | 0.034 |
| 2 (contr.) | 0.5 | 7.100 | 10.900 | 2.610 | 40.800 | 0.054 |
| 3 (contr.) | 0.5 | 6.820 | 9.760 | 3.050 | 21.300 | 0.031 |
| 4 (contr.) | 7.0 | 6.620 | 11.800 | 5.160 | 11.200 | 0.041 |
| 5 (contr.) | 7.0 | 7.040 | 13.500 | 2.790 | 11.400 | 0.033 |
| 6 (contr.) | 7.0 | 8.020 | 11.100 | 2.410 | 10.100 | 0.015 |
| 7 non treated | — | 7.970 | 10.500 | 3.830 | 47.400 | 0.045 |
| 8 non treated | — | 7.270 | 11.400 | 2.780 | 10.800 | 0.022 |
| 9 non treated | — | 7.250 | 10.600 | 3.000 | 44.700 | 0.020 |
| 10 | 0.5 | 7.300 | 11.500 | 3.240 | 12.300 | |
| 11 | 0.5 | 8.270 | 12.300 | 3.440 | 45.100 | 0.019 |
| 12 | 0.5 | 6.560 | 10.500 | 2.730 | 11.800 | 0.030 |
| 13 | 1.0 | 7.880 | 10.600 | 3.360 | 11.300 | 0.048 |
| 14 | 1.0 | 7.300 | 11.200 | 3.110 | 9.520 | 0.060 |
| 15 | 1.0 | 7.350 | 10.700 | 3.850 | 40.200 | 0.019 |
| 16 | 3.0 | 8.130 | 10.800 | 2.900 | 47.600 | 0.195 |
| 17 | 3.0 | 8.340 | 11.000 | 2.870 | 45.400 | 0.184 |
| 18 | 3.0 | 7.060 | 11.300 | 3.150 | 37.800 | 0.131 |
| 19 | 5.0 | 8.200 | 11.100 | 3.070 | 49.900 | |
| 20 | 5.0 | 7.240 | 11.100 | 3.950 | 46.700 | 0.186 |
| 21 | 5.0 | 7.140 | 9.950 | 3.740 | 41.300 | 0.247 |
| 22 | 8.0 | 8.090 | 11.600 | 4.020 | 40.600 | 0.206 |
| 23 | 8.0 | 8.770 | 11.800 | 3.380 | 44.600 | 0.266 |
| 24 | 8.0 | 7.120 | 11.800 | 2.720 | 47.800 | 0.203 |

We claim:

1. A method of administering of a pharmaceutically active substance which does not elicit an immunogenic response to a patient in need thereof, said method comprising the step of administering the pharmaceutically active substance in a carrier, said carrier comprising a deadjuvanted matrix which is a complex of a sterol and one or more saponins which lack adjuvant effect, said matrix comprising spherical nanoparticles formed from annular subunits, each annular subunit being formed from said sterol and said one or more saponins lacking adjuvant effect.

2. A method according to claim 1, wherein said sterol is cholesterol.

3. A method according to claim 1, wherein the matrix also comprises one or more lipids other than said sterol.

4. A method according to claim 3, wherein the one or more other lipids are phospholipids.

5. A method according to claim 1, wherein the carrier particles have a size of 30–50 nm.

6. A method according to claim 5, wherein the carrier particles have a size of 40 nm.

7. A method according to claim 1, wherein the matrix is formed from cholesterol and the saponin B4b or LT 15 and in addition comprises a phospholipid.

8. A method according to claim 7, wherein the matrix is formed from cholesterol and the saponin B4b or LT 15 in combination with the saponin B2 or LT 17.

9. A method according to claim 3, wherein the phospholipid is a phosphatidylethanolamine or phosphatidylcholine.

10. Drug carrying particle comprising a deadjuvanted matrix which is a complex of a sterol and one or more saponins which lack adjuvant effect as a carrier to which has been connected a pharmaceutically active substance which does not elicit an immunogenic response, which particle is formed from annular subunits, each annular subunit being formed from said sterol and said one or more saponins lacking adjuvant effect.

11. Drug carrying particle according to claim 10, wherein said sterol is cholesterol.

12. Drug carrying particle according to claim 10, wherein the matrix also comprises one or more lipids other than said sterol.

13. Drug carrying particle according to claim 12, wherein the one or more other lipids are phospholipids.

14. Drug carrying particle according to claim 10, wherein the spherical particle has a size of 30–50 nm.

15. Drug carrying particle according to claim 14, wherein the spherical particle has a size of 40 nm.

16. Drug carrying particle according to claim 10, wherein the pharmaceutically active substance has been connected to the matrix by covalent or hydrophobic bonds.

17. Drug carrying particle according to claim 10, wherein the pharmaceutically active substance is $CoQ_{10}$.

18. Drug carrying particle according to claim 10, wherein the pharmaceutically active substance is amfotericin B.

19. A pharmaceutical composition comprising drug carrying particles according to claim 10 in combination with a pharmacologically acceptable vehicle.

* * * * *